United States Patent [19]

Haaga

[11] Patent Number: 4,838,280

[45] Date of Patent: Jun. 13, 1989

[54] HEMOSTATIC SHEATH FOR A BIOPSY NEEDLE AND METHOD OF USE

[76] Inventor: John R. Haaga, 3409 N. Hilltop, Chagrin Falls, Ohio 44022

[21] Appl. No.: 199,130

[22] Filed: May 26, 1988

[51] Int. Cl.⁴ .............................................. A61B 10/00
[52] U.S. Cl. .................................................. 128/751
[58] Field of Search ................. 128/305, 349, 351–355

[56] References Cited

U.S. PATENT DOCUMENTS

| | | | |
|---|---|---|---|
| 2,814,296 | 11/1957 | Everett | 128/339 |
| 3,106,483 | 10/1963 | Kline et al. | 117/62.2 |
| 3,358,684 | 12/1967 | Marshall | 128/214.4 |
| 4,650,488 | 3/1987 | Bays et al. | 623/12 |
| 4,708,147 | 11/1987 | Haaga | 128/753 |

*Primary Examiner*—Max Hindenburg
*Attorney, Agent, or Firm*—Body, Vickers & Daniels

[57] ABSTRACT

A hemostatic gelatin sheath is fitted as a portion of an outer cannula over the distal portion of the inner cutting channula of a biopsy needle. Positioning means associated with the cannulas accurately deposits the hemostatic sheath at the position where the biopsy specimen was taken and the needle with the specimen therein is then withdrawn. The in situ sheath minimizes bleeding from the biopsy site before the gelatin is absorbed by the body.

19 Claims, 2 Drawing Sheets

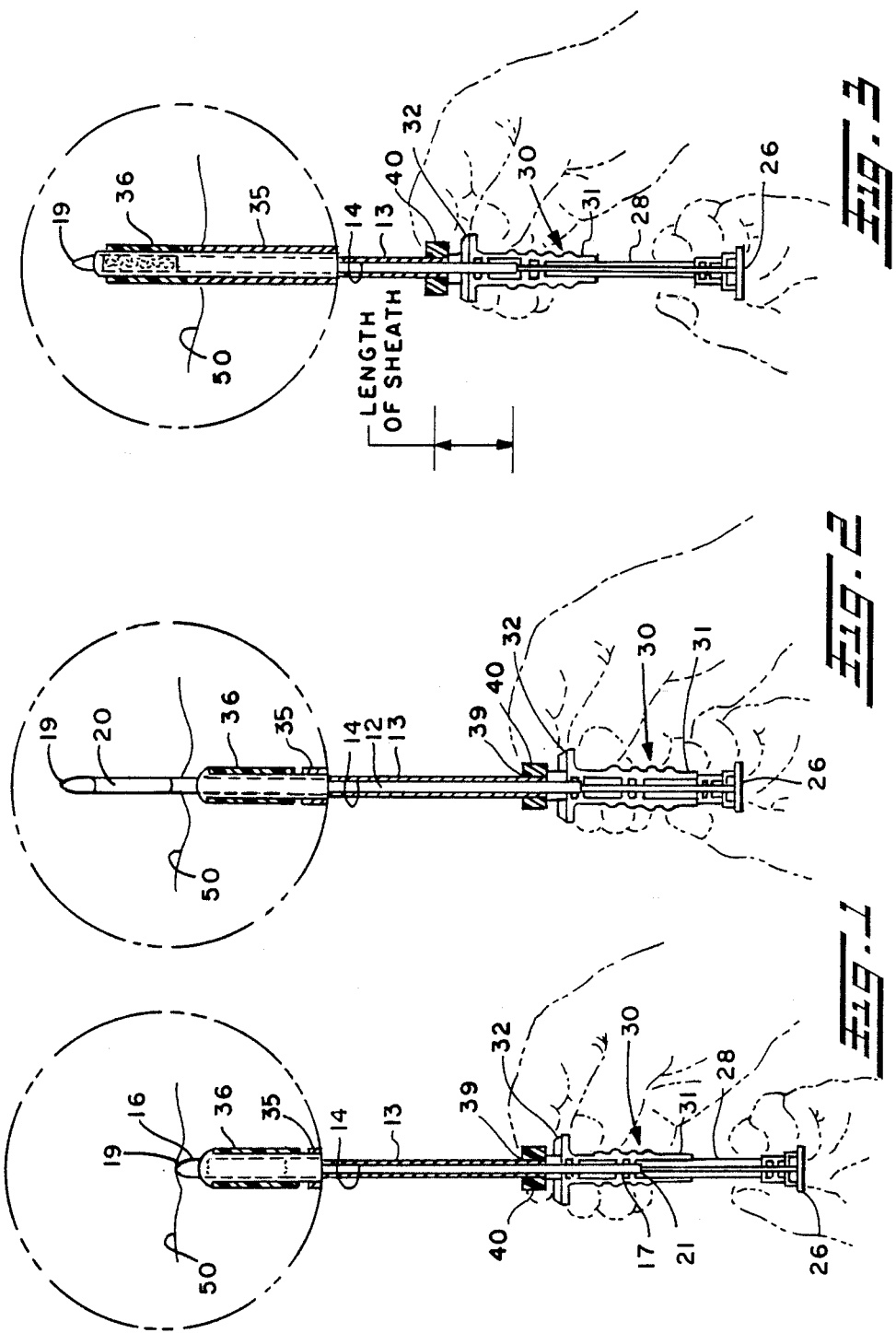

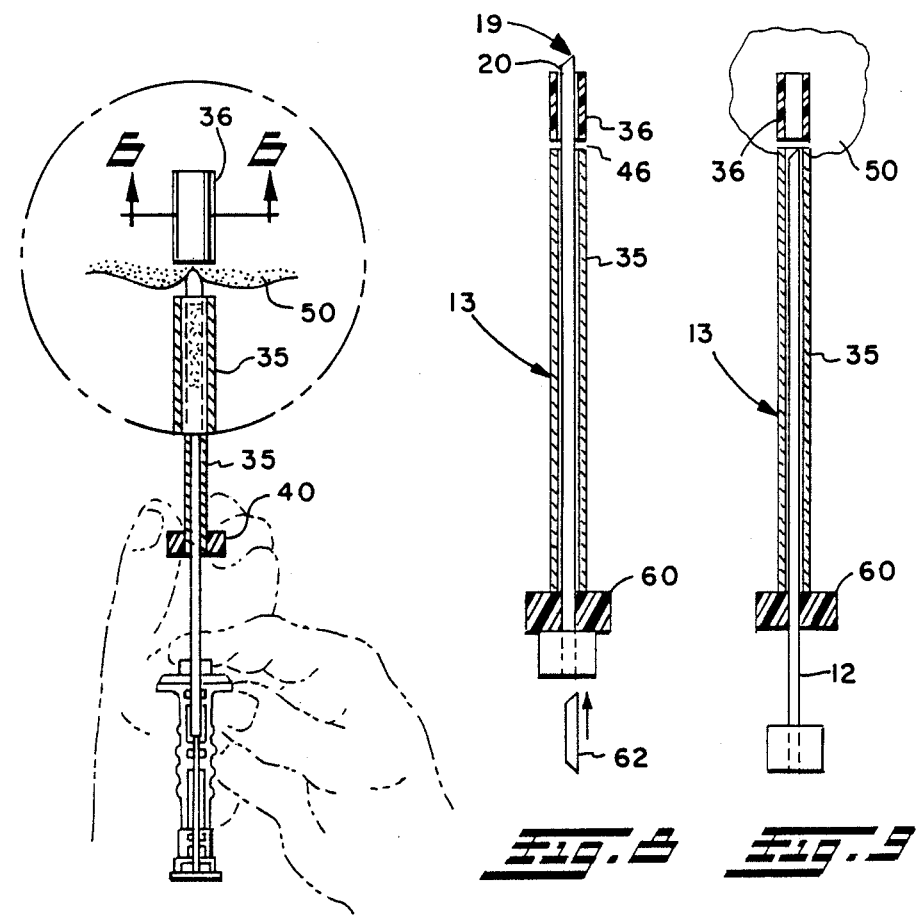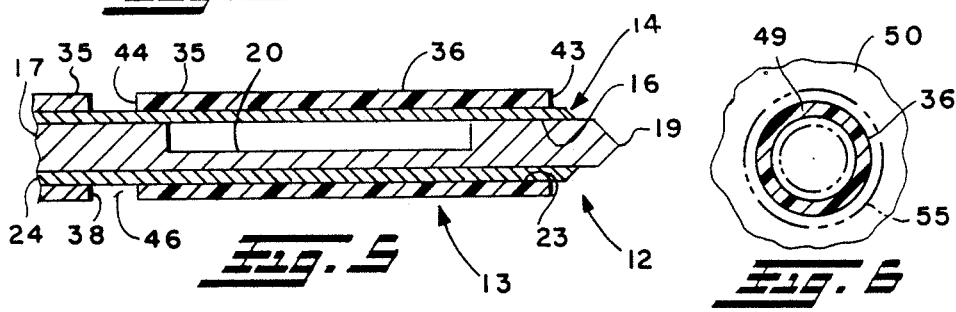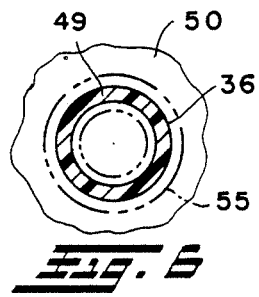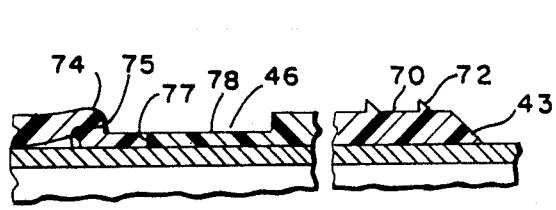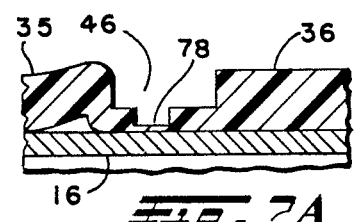

HEMOSTATIC SHEATH FOR A BIOPSY NEEDLE AND METHOD OF USE

This invention relates generally to surgical needles and more particularly to a biopsy needle construction and a method for performing a biopsy using the needle construction which minimizes hemorrhagic complications.

The invention is particularly applicable for removing tissue and like specimens from the human body and will be described particular reference thereto. However, it will be appreciated by those skilled in the art that the invention has broader application and may be used for selective extraction of tissue samples and the like from other living matter, such as animals, and conceptually is applicable in a broad sense to any surgical procedure requiring insertion of instruments and the like into any organ where the tissue may be punctured.

INCORPORATION BY REFERENCE

U.S. Pat. No. 4,708,147 dated Nov. 24, 1987; U.S. Pat. No. 3,358,648 dated Dec. 19, 1967 and U.S. Pat. No. 3,106,483 dated Oct. 8, 1963 are incorporated by reference herein.

BACKGROUND

Generally speaking, biopsy needles fall into one of two types, an end cutting needle, commonly referred to as a "Menghini" needle, or, a side cut needle such as the type commercially known as "Tru-cut" needles. Fundamentally, an end cutting needle includes a hollow cutting cannula having an especially configured, circumferentially sharpened, open end at the distal portion thereof. A stylette is conventionally inserted into the hollow shaft of the cannula in its "at rest" or unactuated position and generally extends flush with the open cutting edge of the cannula to close the open end. With the stylette thus inserted, the end cutting needle is inserted into the patient until the needle reaches the site of the lesion where the biopsy specimen is to be taken. The stylette is withdrawn and the needle further inserted into the lesion with the result that tissue is cut and fills the now open cutting end of the cannula as it travels a slight distance through the lesion to collect the specimen. A suction device can be applied to the proximal portion of the cannula to withdraw the tissue sample thus taken. Alternatively, the cannula can be rotated to sever the tissue and the cannula withdrawn from the site. In a typical side cut needle, there is a "solid" inner cannula within an outer cannula and the inner cannula has a shaped pointed end with a cutting groove formed in the distal portion of the inner cannula behind the pointed end. The side cut needle is inserted into the patient until the needle reaches the site of the lesion where the biopsy sample is to be taken. The inner cannula is then advanced into the lesion to the point where the specimen is to be taken and rotated so that the cutting groove severs the tissue. The outer cannula advances over the inner cannula thus containing or entrapping the specimen within the groove of the inner cannula and the outer cannula, and the needle is then withdrawn from the site. There are many biopsy needle designs commercially available or described in the literature. For example, it is known to provide an inner cannula within the cutting cannula of the end cutting needle which uses movable jaws extending beyond the distal end of the cutting cannula to sever and extract the biopsy specimen. "Hybrid" cannulas are also known. Fundamentally, if the biopsy specimen is removed through the cutting end of the cannula it is known and will be referred to hereinafter as a "end-cutting" needle and if the sample is taken from the side of the needle, the needle will be referred to hereinafter as a "side-cutting" needle. The invention described herein is applicable to all end-cutting and side-cutting biopsy needles.

Because most biopsy needles reliably function to remove biopsy specimens, the major concern today with biopsy needles and the procedures governing the use thereof centers about hemorrhaging complications caused by or attributed to the biopsy. The complications arise from severing blood vessels while positioning the needle and while severing the specimens and the resultant bleeding caused thereby. To accurately guide the biopsy needle, percutaneous procedures have been developed to permit visual radiological observation of the instrument inside the body. In conjunction with CT guided biopsies, biopsy needles have been especially designed to provide good CT scanning images. An example of such a needle is disclosed in my earlier U.S. Pat. No. 4,708,147 dated Nov. 24, 1987 incorporated herein by reference. The reader may refer to may prior patent for a more detailed explanation of various hemorrhagic complications resulting from the organ from which the biopsy specimen is taken.

It is difficult to accurately estimate the incident rate of hemorrhagic complications with conventional biopsy needles because of the variations of the needle designs in use, the patient selection and the somewhat different biopsy techniques employed. However, support within the literature can be found for quoting a five percent (5%) complication rate in blind liver biopsies which may be perhaps even higher for blind kidney biopsies. In my studies of guided biopsies using image scanning techniques, I would estimate the complication rate to drop to about 1.5%. While this represents a significant decrease, this problem, to which my invention is directed, is not resolved.

Within the prior art, the use of gelatin as a substance for making medication capsules for internal use and adapted to be absorbed by enzyme action or other physiological processes within the body is well known. Also, the use of gelatin material for various surgical techniques has been well documented. In particular, the use of a gelatin material in a "sponge" form or as a foam is commercially available from the Upjohn Company under the trademark "Gelfoam". Gelfoam with and without thrombin, a protein which is active at the last stage of clot formation and functions to change fibrinogen to fibrin, has been used in surgery in virtually all organ systems including prostrate, brain, musculoskeletal, vascular graphs and other areas without adverse complications. The use of gelatin as a coating for a fabric, blood-vessel graft is disclosed in U.S. Pat. No. 3,106,483 to Kline et al dated Oct. 8, 1963, incorporated herein by reference.

The use of hardened gelatin as forming a part of a surgical instrument is disclosed in U.S. Pat. No. 3,358,684 to Marshall dated Dec. 19, 1967, incorporated by reference herein. In Marshall, the distal cutting edge of a cannula which is used as a parenteral injection device is formed from a thiolated gelatin material. Specifically, the gelatin distal tip punctures a vein, and eventually dissolves, leaving the proximal portion of the cannula within the vein for administrating parenteral solutions. The cannula can be thus left in situ without vein damage which would otherwise arise from the presence of a sharp needle or the removal of the needle. In this sense, the prior art recognizes that it is known to use gelatin as a surgical instrument which can be dissolved at the insertion site.

SUMMARY OF THE INVENTION

Accordingly, it is a principal object of the invention to provide a needle for biopsy sampling purposes which reduces hemorrhagic complications arising from the puncture site in the organ which result when the biopsy specimen is taken.

This object is achieved in a biopsy needle which may best be explained by the relative position of its parts before, during and after the biopsy is taken. Fundamentally, the needle has an unactuated position defined by the position of its parts prior to insertion of the needle in the patient, an actuated position defined by its parts position when the sample is being taken and a retracted position defined again by the position of its parts when the needle is removed from the biopsy site. Generally speaking, the needle of the present invention has an inner cutting cannula (which may or may not be hollow depending upon the type of needle) having a distal portion for insertion into the biopsy site and a contiguous proximal portion extending from the distal portion. The distal portion in turn is defined as that length of the inner cannula which is inserted into the patient in the actuated position of the needle and the distal portion carries the means for taking the biopsy sample, i.e. side or end cutting. At least one outer hollow cannula coaxial with and receiving the inner cannula is provided. The outer cannula has a proximal portion and a separable distal portion. Positioning means associated with the proximal portions of either the inner or outer cannulas or both are manipulated by the physician as the needle is inserted into the site, the biopsy taken and the needle retracted so that the distal portion of the outer cannula is separated from the proximal portion and remains at the biopsy site when the needle is in its retracted position. The distal portion of the inner cannula is made of a biodegradable gelatin material which acts to minimize bleeding from the biopsy site before the gelatin material dissolves. In accordance with another feature of the invention, the gelatin material can include the protein thrombin as one of the substance thereof which enhances or increases tendency of the blood emanating from the biopsy site to clot.

In accordance with another features of the invention, the outer cannula of the present invention either replaces the outer cannula of the existing biopsy needle, such as the Menghini end cutting needle, or is an additional cannula receiving the existing outer cannula (now intermediate cannula) of the existing biopsy needle, such as the Tru-Cut side cutting needle. Accordingly, the concept of an outer cannula containing, as the distal portion thereof, a detachable sheath, positioned in situ by the outer cannula expands the potential application of the hemostatic sheath to other surgical type instruments such as scopes which are designed to puncture an organ.

In accordance with still another aspect of the invention, in the unactuated position of the biopsy needle, the distal portion of the outer cannula, i.e., the hemostatic sheath, fits over the inner cannula but is spaced from the distal end of the proximal portion of the outer cannula. The presence of the space or gap forms part of the positioning means associated with the needle to assure the surgeon, especially for blind biopsies, that the hemostatic sheath, in the needle retracted position, has separated from the inner cannula.

In accordance with an essential feature of the invention, the cross sectional area of the hemostatic sheath is larger than the cross sectional area of the puncture formed by the inner cannula. When the hemostatic sheath is positioned by the positioning means at the biopsy site, the outer surfaces of the hemostatic sheath compress the bleeding tissue surrounding the biopsy site to minimize bleeding from the organ. Within several seconds, the sheath absorbs body fluid and begins to swell increasing the tamponade effect to occlude the flow of blood from the site. Additionally, it is believed that because the hemostatic sheath is a foreign body, the sheath acts as a nidus for platelet aggregation which assists in blood clotting whether or not thrombin is added as one of the substances of the gelatin material of the sheath. By this geometric arrangement, a known substance, gelatin, is used to prevent bleeding before it harmlessly dissolves, in a conventional manner, within the body.

In accordance with a more specific feature of the invention, the hemostatic sheath's outer cylindrical surface has tiny radially outward projections or barbs extending therefrom which prevents the hemostatic sheath from leaving the biopsy site when the inner cannula is retracted. Other modifications to the configuration of outer cannula, including the sheath are disclosed, for purposes of enhancing the positioning means of the needle. Specifically, the gap referred to above is maintained throughout the needle insertion to provide the surgeon with a sensitory feel indicating proper positioning of the sheath within the lesion.

Still yet another specific feature of the invention is attributed to the fact that the gelatin material of the hemostatic sheath develops a low coefficient of friction when the material is moist or wet while the material is hard when dry. The low coefficient of friction of the sheath, permits the sheath to be easily inserted in the biopsy site, and the inner cannula retracted, while the hemostatic sheath, in its hard state, can be sized for application to the inner cannula to define the aforementioned gap in the unactuated position of the needle.

In accordance with a broader feature of the invention, a method for performing a biopsy using a hemostatic sheath is disclosed. The method broadly comprises manipulating the cannulas of a biopsy needle to achieve the aforedescribed positions of the needle to insure accurate placement of the hemostatic sheath within the biopsy site to avoid hemorrhagic complications.

In accordance with still another aspect of the invention, the sheat conceivably could function, in addition to its hemostatic purpose, as a vent for purposes of initially admitting or directing gases from the penetrated or biopsied organ therethrough in a harmless manner. Conceptually, the sheath could prevent the lung from inadvertently collapsing during a biopsy.

It is thus an object of the invention to provide a hemostatic sheath for use with any biopsy needle which sheath is deposited at the biopsy site to prevent bleeding therefrom.

It is another object of the invention to provide a method for taking a biopsy specimen which deposits a hemostatic sheath at the biopsy site.

Still another object of the invention is to provide a biopsy needle which can accurately position, in situ, a portion of the needle which acts as a hemostatic sheath.

Still another object of the invention is to provide a modified biopsy needle which permits placement of a hemostatic sheath within the biopsy site in a relatively easy manner and without undue resistance.

Still another feature of the invention is to provide a biopsy needle which can be readily mass produced without undue expense.

Still yet another object of the invention is to provide a hemostatic sheath which can be readily applied to any conventional biopsy needle.

A still further object of the invention is to provide a sheath for use with any surgical instrument which penetrates an organ to enhance blood clotting and avoid hemorrhagic complications arising from use of the instrument.

Another object of the invention is to provide a sheath for use with any instrument and a method for use thereof which positions the sheath at the site of the puncture to prevent hemorrhagic complications arising from the puncture, and also, in certain applications, to provide an initial vent fro directing gases from the punctured organ in a harmless manner.

Further objects and advantages of the invention will become apparent to those skilled in the art from reading and understanding the following detailed description of species thereof and from the accompanying drawings which illustrate preferred embodiments that the invention may take in physical form and in certain parts and arrangement of parts.

BRIEF DESCRIPTION OF THE DRAWINGS

FIGS. 1 through 4 show the invention applied to a side-cutting biopsy needle and the various positions of the needle as the biopsy is taken;

FIG. 5 is a cross sectional view principally of the distal portion of the needle shown in FIGS. 1-4;

FIG. 6 is a cross sectional view of the invention shown in an in situ position;

FIGS. 7 and 7a are cross sectional views of various portions of the distal portion of a biopsy needle of the end cutting type illustrating various embodiments of the invention; and FIGS. 8 and 9 show the invention applied to an end-cutting biopsy needle.

DETAILED DESCRIPTION OF THE INVENTION

Referring now to the drawings wherein the showings are for the purpose of illustrating preferred embodiments of the invention only and not for the purpose of limiting the same, there is shown in FIGS. 1-5 and 8-9 a biopsy needle 10 generally defined as comprising an inner or cutting cannula 12 which is coaxially received within an outer cannula 13. Cutting cannula 12 has a distal portion 16 and contiguous therewith a main or proximal portion 17. Distal portion 16 has an entry end 19 so that needle 10 can enter or puncture the site of the biopsy and a cutting edge 20 which functions to sever the tissue in the lesion for collecting a biopsy sample.

For the side-cutting needle illustrated in FIGS. 1-5, and as best shown in FIG. 5, cutting 12 is shown as a solid, cylindrical member co-axially received, in a conventional telescoping manner, within an intermediate cannula 14. Intermediate cannula 14 is co-axially received within outer cannula 13, but as will be noted hereafter, does not telescopically move in a significant manner relative to outer cannula 13. For orientation purposes, intermediate cannula 14 has a distal end 23 and a proximal end 24. The entry end 19 of cutting cannula 12 is shaped as a pointed end and cutting edge 20 is defined by the wall edges of the cannula left after a circumferentially and longitudinally extending segment has been removed from cutting cannula 12. The exposed wall edges or cutting edges 20 of cutting cannula 12 are sharpened in accordance with normal practice. For definitional purposes, distal portion 16 is defined as that body portion of cutting cannula 12 which extends from entry end 19 to the end of cutting edge 20, and proximal portion 17 is contiguous with and extends therefrom. The term "cutting cannula" is meant to apply to all biopsy needles or medical instruments to which an outer sheath can be fitted for purposes of working the invention as described hereafter. Thus, cutting cannula 12 is meant to include an does include various accessories normally used with the cannula such as a stylette, if one is to be used, or vacuum appendages associated with cutting cannula 12 for extracting the biopsy sample. Also meant to be included within the term "cutting cannula" are end cutting biopsy needles which have movable jaws at the entry end or hybrid biopsy needles such as the type disclosed in may prior patent referred to above.

Referring now to FIGS. 1-4, proximal portion 17 of cutting cannula 12 is attached to a positioning mechanism which is shown in its fundamental, simplest form for ease in explanation. It is contemplated that spring actuated positioning mechanisms now developed for conventional biopsy needles can be modified by those skilled in the art to provide the desired needle positioning as illustrated in the drawings which is achieved by hand manipulation. The bottom end 21 of proximal portion 17 of cutting cannula 12 is fixed or rigidly connected to an obturator having an obturator handle 26 and an "X"-shaped plunger portion 28 which is telescopically received within a stem 30 having a base portion 31 ending in a configured easily grippable cannula handle 32. Plunger portion 28 has a length at least equal to the length of the distal portion 16 of cutting cannula 12. As shown in FIGS. 1-4, by grasping cannula handle 32 and obturator handle 26, the surgeon can move cutting edge 20 to a forward or retracted position relative to outer cannula 13 and intermediate cannula 14. Not shown, but contemplated as being attached to cutting cannula 12 either at proximal portion 17 or to obturator 25 for actuation at some position thereof, may be a vacuum conduit for applying suction to the interior of cutting cannula 12 for purposes of removing the biopsy specimen taken or assuring positioning of the biopsy specimen within cutting cannula 12. As described thus far, the biopsy needle 10 is somewhat conventional as is the positioning mechanism.

Cutting cannula 12 is telescopically received within intermediate cannula 14 which is then co-axially received within an outer sheath or outer cannula 13. Outer cannula 13 has two separate or separable portions defined as a proximal portion 35 and a distal portion 36. Proximal portion 35 in turn has a distal end 38 adjacent distal portion 36 and a proximal end 39 at the opposite end thereof which is fixedly secured as by glue to a pusher handle 40 of the positioning means. Similarly, proximal end 24 of intermediate cannula 14 is likewise fixed to pusher handle 40. Thus intermediate and outer cannulas 14, 13 move as a unit. Accordingly, when movement of the side cutting needle of FIGS. 1–5 will be explained, reference will only be made to outer cannula 13, it being understood that intermediate cannula 14 will similarly move therewith. As can be seen from FIGS. 1–4, pusher handle 40 can telescopically move outer cannula 13 relative to cutting cannula 12. Proximal portion 35 can be constructed from any suitable plastic material or metal such as stainless steel, or preferably, a biodegradable gelatin material such as Gelfoam.

Referring now to FIG. 5 and in the preferred embodiment of the invention, distal portion 36 of outer cannula 13 is a separate, generally cylindrical mass of biodegradable gelatin adjacent proximal portion 35 of outer cannula 13 and as noted proximal portion 35 and distal portion 36 together, for definitional purposes, comprise outer cannula 13. Distal portion 36 alternatively may be referred to as a hemostatic sheath and the two terms will be used interchangeably throughout the specifications. As noted above, hemostatic sheath 36 is made of a conventionally available biodegradable gelatin with either a pork or beef base with conventional additives depending upon the dissolution time desired for sheath 36. An acceptable gelatin material which is available in a foam or sponge form from the Upjohn Company under the trademark Gelfoam. The Gelfoam material would have to be made in hardened form. An acceptable hardened thiolated gelatin material which could also be used as the sheath material is described in U.S. Pat. No. 3,106,483 dated Oct. 8, 1963.

Hemostatic sheath 36 has an entry end 43 which is the end which first enters the biopsy site and a proximal end 44 which is adjacent distal end 38 of proximal portion 35. The length of hemostatic sheath 36 may vary depending upon the biopsy taken, but as a minimum, the length of hemostatic sheath 36 should preferably be as long as the length of the biopsy speciman taken. For cutting cannula 12 of the side cutting type in FIG. 5, the length of hemostatic sheath 36 should probably be at least equal to the length of cutting edge 20. In the unactuated, "at rest" or uninserted position of needle 10, proximal end 44 of hemostatic sheath 36 is spaced a slight distance away from distal end 38 of proximal portion 35 to define a circumferentially extending gap or space 46 existing between distal and proximal portions 35, 36. In practice, gap 46 can occur by simply sizing the inside diameter of hemostatic sheath 36 relative to the outside diameter of distal portion 16 of cutting cannula 12 so that hemostatic sheath 36 can initially slide onto cutting cannula 12 when wet. Alternatively, the inside diameter of hemostatic sheath 36 could be formed with a slight taper increasing the sheath's fit at proximal end 44 thus maintaining gap 46. When so constructed, gap 46 will decrease when hemostatic sheath 36 is inserted into the biopsy site. Two additional modifications are shown in FIGS. 7 and 7a and described hereafter which can be employed to positively maintain gap 46 if desired.

Entry end 43 of hemostatic sheath 36 is preferably formed as a flat surface perpendicular to the length of hemostatic sheath 36 as shown in FIG. 5, or alternatively, depending upon the hardness of the lesion at the site where the biopsy is to be taken (i.e. bone marrow) entry end 43, could be tapered as shown in FIG. 7. Also, the edge surface 45 of entry end 43 will generally lie in one plane, although edge surface 45 could assume a curvilinear or tapering configuration. However, because the coefficient of friction of the gelatin of hemostatic sheath 36 is reduced when wet and hemostatic sheath 36 will be wet as it enters the biopsy site and encounters bleeding from the site, it is not believed necessary to form edge surface 45 as a cutting edge. In point of fact it is desired that edge surface 45 not act as a cutting edge such as is necessary in Marshall's patent because the tissue surrounding the biopsy specimen is to be displayed and compressed by the outer cylindrical surface of hemostatic sheath 36. If the tissue is again cut by edge surface 45 further bleeding will ensue. Thus, the particular type of biopsy and the hardness of the lesion at which the biopsy is taken, will determine the exact shape of entry end 43 and edge surface 45 but the shape will be such as to permit compression of the tissue at the biopsy site while permitting easy entry of hemostatic sheath 36 into the lesion.

Referring now to FIGS. 1–4, the unactuated position of biopsy needle 10 is shown in FIG. 1. In this position cutting edge 20 of cutting cannula 12 is adjacent tissue 50, pusher handle 40 is against cannula handle 32 and plunger portion 28 is in a retracted position. Maintaining cannula handle 32 and pusher handle 40 at approximately the same elevation, obturator handle 26 is slid into stem 30 so that distal portion 16 of cutting cannula 12 enters lesion 50 whereat the biopsy is taken in the normal manner (FIG. 2). (If biopsy needle 10 was equipped with a stylette the stylette would have been removed while cutting cannula 12 was moved in lesion 50 to the site of the biopsy sample.) The cannula is then rotated in the convention manner to permit cutting edge 20 to extract the biopsy sample or specimen. (Additionally, a vacuum could be applied to the inside diameter of cutting cannula 12.) In any event, when the biopsy specimen is taken or is physical severed and within cutting cannula 12, needle 10 is actuated into its retracted position. For a side cutting biopsy needle two steps are required to reach the retracted position. With the obturaor handle 26 maintained at approximately the same position, pusher handle 40 and cannula handle 32 are grasped and moved together. Proximal portion 35 contacts hemostatic sheath (reducing gap 46) and slides hemostatic sheath 36 over cutting cannula 12 to again cover distal portion 16 of cutting cannula 12 (FIG. 3). Intermediate cannula 14 is likewise disposed over cutting cannula 12 as in the conventional mode. Again, the positioning mechanism shown, less outer cannula 13 is conventional.

When hemostatic sheath 36 travels into the biopsy site, the tissue in the site is compressed. That is, when the biopsy specimen was taken, a generally cylindrically shaped void was created in lesion 50. The surface of the tissue defining the void shape contains blood vessels which were severed by needle 10. Because of the geometric arrangement of cutting cannula 12 and hemostatic sheath 36, the cross-sectional diameter of the void is approximately equal to the inside diameter of hemostatic sheath 36. Thus, the cross-sectional area of hemostatic sheath 36 as shown in FIG. 6, forms an annulus the outer surface 46 of which displaces the tissue containing the severed blood vessels and that tissue is being compressed as it is being displaced and the compression acts to retard bleeding. Also, gap 46 gives a slight sensation felt in pusher handle 40 and cannula handle 32 by the surgeon to indicate that the sheath has travelled to almost its exact position within the biopsy site. This is helpful when conducting blind biopsies. This also ensures lengthwise positioning of hemostatic sheath 36.

In the second step necessary to reach the retracted position (FIG. 4), pusher handle 40 is maintained at the same position and cannula handle 32 is moved or retracted until obturator handle 26 contacts base portion 31 whereat needle 10 is removed with the biopsy specimen intact. The presence of gap 46 provides a lost motion type of connection which insures that inner cannula 12 reaches its retracted position and thus separates hemostatic sheath 36 at the biopsy site (the lost motion resulting from diminution of gap 46 is more readily discernible with respect to the end cutting needle shown in FIGS. 8 and 9). That is, when obturator handle 26 moved distal portion 16 of cutting cannula 12 into lesion 50, it traveled a fixed axial distance. When hemostatic sheath 36 was moved over distal portion 16 of cutting cannula 12, cannula handle 32 and pusher handle 40 moved the fixed axial distance plus the distance of gap 46. This increased the length of plunger portion 28 extending from stem 30 the axial distance of gap 46. When cutting cannula 12 is retracted from lesion 50 in FIG. 4, the plunger distance is then taken up when obturator handle 26 contacts stem 30 to insure separation of hemostatic sheath 36 from needle 10.

Referring now to FIGS. 8 and 9, an end cutting biopsy needle 10 is provided with a hemostatic sheath 36 and like parts will be designated by like numbers where possible. In the end cutting or Menghini needle configuration of FIGS. 8 and 9, obturator 25 is replaced by a hub member 60 affixed to bottom end 29 of cutting cannula 12. Hub 60 can be hollow for insertion of a stylette 62. The hemostatic sheath 36 is inserted over cutting cannula 12 with gap 46 as described for side cutting biopsy needle 10 of FIGS. 1–5. FIG. 8 illustrates end cutting biopsy needle 10 in its unactuated position, it being assumed that stylette 62 is inserted within cutting cannula 12 to provide a solid entry end 19, and the circumferential edge of entry end 19 is formed as cutting edge 20. With stylette 62 inserted, pusher handle 40 and hub 60 are held together and end cutting biopsy needle 10 inserted in the unactuated position in lesion 50 to a point just before the biopsy specimen is to be taken. At this position (not shown) stylette 62 is removed and cutting and outer cannulas 12, 13 are moved, without relative movement, (i.e. pusher handle 40 and hub member 60 together) while the biopsy is taken through entry end 19 of cutting cannula 12 in the normal fashion. The length of hemostatic sheath 36 will at least preferably be equal to the travel of needle 10 with stylette 62 removed. Thus, the actuated position and unactuated position of end cutting biopsy needle 10 are generally the same (less the take-up in gap 46). After the biopsy specimen is collected through vacuum or through the motion of needle 10 vis-a-vis rotation of cutting edge 20, pusher handle 40 is maintained in the same position as in the actuated position and hub member 60 is moved to a retracted position (FIG. 8). As in FIG. 4, this motion places hemostatic sheath 36 at the site where the biopsy specimen was taken and insures (as was done for the side needle) that entry end 19 of cutting cannula 12 is within proximal portion 35 of outer cannula 13.

It is believed that the hemostatic effect resulting from the precise, in situ placement of hemostatic sheath 36 occur as a result of several factors. First, there is a blood clotting attributed to the mechanical insertion of hemostatic sheath 36. As noted above, when cutting cannula 12 extracts the biopsy specimen, the tissue is cut and vessels are severed at the edge of the tissue which borders on the margin of the tissue core. As shown in FIG. 6, when hemostatic sheath 36 is properly positioned, entry end 43 pushes against the edge of the tissue which as been cut by cutting cannula 12. This provides a compression of the tissue which is bleeding simply because the cross-sectional area of hemostatic sheath 36 circumscribes and thus compresses the bleeding surface. This tends to stop the surfaces from bleeding. Importantly, within a few seconds and for a long as a few minutes, the gelatin will absorb the blood and swell and thus expand both externally and internally to occupy the space indicated by the dotted lines 55 shown in FIG. 6. This produces a tamponade effect further acting to occlude the hole in the tissue and any vessels in the area. Finally, hemostatic sheath 36 in the plain gelatin form is a foreign body which acts as a nidus for platelet aggregation and stimulates blood clotting. All of these factors will act to reduce hemorrhagic complications when hemostatic sheath 36 is formed from a plastic, biodegradable gelatin without any additional additives or substances added to the gelatin. By the time the hemostatic sheath is absorbed or dissolved within the body, the bleeding from the biopsy site will have stopped.

In order to enhance the last mentioned feature, and as noted above, thrombin can be added as one of the component substances of the gelatin material of hemostatic sheath 36. As is known, thrombin is a protein which is active at the last stage of clot formation and functions to change fibrinogen to fibrin. Because hemostatic sheath 36 with thrombin added is very thromgenic, hemostatic sheath 36 is also very active at the very last phase of blood clotting. Thus, deficiencies and coagulation factors such as factor VIII, prothrombin which occurs with liver disease, etc., do not interfere with the blood clotting formation. Additionally, using thrombin as the substance of hemostatic sheath 36 will provide active receptors which attract platelets and improve the aggregation of platelets. Thus, a small amount of thrombin when employed in hemostatic sheath 36 can almost be effective to eliminate clotting factors from any cause. Considering the intense forms of therapy now used in oncology, the significance of the invention in reducing pain and suffering of the patient and the potential life saving implications thereof should not be underestimated.

While the invention has been described in its broad sense, there are several modifications and alterations which can be made to enhance the mechanical performance of biopsy needle 10 employing hemostatic sheath 36. A schematic illustration of several modifications are shown in FIGS. 7 and 7a. In FIG. 7, the outer circumferential surface 70 of hemostatic sheath 36 can be formed with protrusions 72 which are shaped in the form of barbs permitting ingress of hemostatic sheath 36 into the site of the biopsy while preventing egress therefrom.

Another modification shown in FIG. 7 is that distal end 38 of proximal portion 35 of outer cannula 13 can be made of a resilient plastic type material with an offset 74 at distal end 38 which brings distal end 38 slightly away from the outer cylindrical surface 75 of cutting cannula 12. When entry end 19 of cutting cannula 12 is retracted, offset 74 will snap over entry end 19. This snapping action will clearly indicate to the surgeon that biopsy needle 10 is in its retracted position and consequently, hemostatic sheath 36 properly positioned in the biopsy site. This provides a positive sensitory feel to the surgeon through needle 10, which is helpful when conducting blind biopsies. In connection with or without use of offset 74, it is possible to neck down distal end 38 of proximal portion 35 as at 77 and proximal end 44 of hemostatic sheath 36 as at 78 to provide a stationary gap 46 while maintaining a columnar relationship between proximal portion 35 and distal portion or hemostatic sheath 36 of outer cannula 13. The stationary gap 46 will be maintained as the hemostatic sheath 36 is positioned over distal portion 16 of cutting cannula 12. Should lesion 50 be harder than the surrounding tissue, a sensory vibration may be felt by the surgeon as gap 46 passes into lesion 50 to assure the surgeon that hemostatic sheath 36 is properly positioned within the biopsy site.

In connection with necked down portion 78 of hemostatic sheath 36, it is also possible to reduce the diameter of a portion thereof to make the same a frangible connection which becomes severed by the snapping action of offset 74 over the entry end 19 of cutting cannula 12 when cutting cannula 12 is moved to its retracted position. This provides a one piece outer cannula 13 which may have assembly and manufacturing advantages over the two piece design illustrated in the other embodiments. The modifications thus described in FIGS. 7 and 7a insure the positive positioning of hemostatic sheath 36 at its correct in situ position. However, it should be noted that the presence of distal portion 35 of outer cannula 13 as illustrated in FIGS. 1–5 and 7 and 8 functions in and of itself to precisely position hemostatic sheath 36.

Thus, it is apparent that many modifications may be incorporated into the hemostatic sheath and the biopsy needle used with the hemostatic sheath without departing from the spirit or the essence of my invention. For example and as alluded to above, the actuating mechanism employed with the biopsy needle to position the sheath can be spring actuated. Conceptually, an outer cannula does not have to be provided for the side cutting needle. The intermediate cannula 14 could have a radial outwardly project rib or seat to receive hemostatic sheath 36. Intermediate cannula 14 with a sheath seat would then function as outer cannula 13. It is my intention to include all such modifications and alterations insofar as they come within the scope of the present invention.

It is thus the essence of my invention to provide a hemostatic sheath for use in a biopsy needle or like instrument to avoid hemorrhagic complications resulting from the surgical procedure using the needle or like instrument.

Having thus defined my invention, I claim:

1. A biopsy neelde for taking a biopsy specimen from a patient, said needle having an unactuated position defined by the relative position of its parts prior to insertion in the patient, an actuated position defined by the relative position of its parts while said specimen is being taken and a retracted position defined by the relative position of its parts when said needle is removed from the site where the biopsy was taken, said needle comprising:

(a) an inner cutting cannula having a distal portion for insertion into said site and a contiguous proximal portion extending from said distal portion, said distal portion defined as that length of said inner cannula which is inserted into said patient in said actuated position, and including means to sever said specimen from said patient;

(b) an outer hollow cannula co-axial with and receiving said inner cannula, said outer cannula having a proximal portion and a separable distal portion, said distal portion being separated from said proximal portion and remaining at said site in said retracted position of said needle;

(c) positioning means associated with said proximal portions of said inner and outer cannulas to cause movement of one of said cannulas relative to the other when said needle moves from one of said positions to the other; and (d) said distal portion of said outer cannula being made of biodegradable gelatin material for minimizing bleeding of said patient from said biopsy site.

2. The biopsy needle of claim 1 wherein said gelatin material includes thrombin as a substance thereof.

3. The biopsy needle of claim 1 wherein said distal portion of said outer cannula has a rear end adjacent said inner cannula's proximal portion when said needle is in its unactuated position and a front end opposite said read end;

said means for severing said specimen leaving a generally cylindrical void in the tissue of the patient;

said distal portion of said inner cannula being generally cylindrical having initially an inside diameter approximately equal to the diameter of said cylindrically shaped void; and said positioning means effective to position said distal portion overlying said void whereby said tissue surrounding said void is compressed to minimize bleeding.

4. The biopsy needle of claim 3 wherein said distal portion swells in size before dissolving in the patient.

5. The biopsy needle of claim 1 wherein said positioning means including at least one barb-like protrusion in said exterior surface of said outer cannula's distal portion for positively retaining said portion in said patient when said needle is in its retracted position.

6. The biopsy needle of claim 5 wherein said positioning means further includes a circumferentially extending space between said distal portion and said proximate portion of said outer cannula for locating the position of said inner cannula at said site in said retracted position of said needle.

7. The biopsy needle of claim 6 further including frangible means connecting said proximate portion of said distal portion of said outer cannula to one another when said needle is in its unactuated position and defining said space, said frangible means severed when said needle is in its retracted position.

8. The biopsy needle of claim 1 wherein said outer cannula comprises a first intermediate hollow cannula and a second larger outer cylindrical cannula co-axial with and receiving said intermediate cannula, said inner cannula telescoping received within said intermediate cannula, said forward end of said inner cannula is preconfigured into a sharpened end for penetrating said patient, said means to sever said sample includes a longitudinally extending sharpened groove in said distal portion of said inner cannula behind said forward end, said groove receiving said specimen in said actuated position.

9. The biopsy needle of claim 8 wherein said means for positioning includes inner cannula means attached to the proximal end of said inner cannula for moving said inner cannula relative to said outer cannula to said actuated position, outer cannula means attached to the proximal end of said outer cannula for moving said outer cannula relative to said inner cannula when said needle is in said actuated position, said inner cannula means further effective with said outer cannula means to deposit said distal portion of said outer cannula at said site in said retracted position.

10. The biopsy needle of claim 1 wherein said forward end of said inner cannula is preconfigured into a hollow sharpened end for penetrating said patient, said end receiving said sample in said actuated position.

11. The biopsy needle of claim 10 wherein said means for positioning further includes cannula means attached to the proximal portion of one of said cannulas to cause said inner and outer cannulas to move together into said actuated position and inner cannula means secured to said inner cannula to cause said inner cannula to axially move relative to said outer cannula into said retracted position.

12. The biopsy needle of claim 1 wherein said proximal portion of said outer cannula is made of biodegradable gelatin material.

13. The biopsy needle of claim 1 wherein said positioning means further includes a circumferentially extending space between said distal portion and said proximal portion of said outer cannula for locating the position of said inner cannula at said site in said retracted position of said needle.

14. A biopsy needle instrument comprising an inner cannula disposed within an outer cannula, said outer cannula having a proximate portion and a removable distal portion, means for depositing said distal portion at the site where said needle punctures an organ after said needle has been removed, said distal portion being of a biodegradable gelatin material to minimize bleeding complications resulting from the use of said needle.

15. The biopsy needle of claim 14 wherein said gelatin material includes thrombin as a substance thereof.

16. The biopsy needle of claim 15 wherein a positioning space exists between said distal and said proximate portions.

17. A method for performing a biopsy comprising the steps of:
providing an inner cutting cannula and an outer hollow cannula co-axially receiving said inner cannula, said outer cannula having a gelatin hemostatic sheath at its distal end adjacent a proximal portion thereof;
moving said inner and said outer cannulas together to a point adjacent the lesion where said biopsy specimen is to be taken;
axially moving said cutting cannula while maintaining said outer cannula stationary to the site where said specimen is to be taken;
severing the specimen at said site and positioning same within said cutting cannula;
maintaining said cutting cannula generally stationary while axially moving said outer cannula to a position whereat said sheath overlies said specimen; and
simultaneously withdrawing said cutting and said outer cannula from said site while leaving said sheath at said site.

18. The method of claim 17 wherein said specimen is severed through the end of said cutting cannula.

19. The method of claim 17 wherein said specimen is severed at the side of said cannula.

* * * * *